United States Patent [19]

Shields

[11] 4,070,756

[45] Jan. 31, 1978

[54] APPARATUS FOR HOLDING HYPODERMIC NEEDLES STRAIGHT AND PLACING SHEATHS THEREON

[76] Inventor: Walter A. Shields, 181-41 Henley Road, Jamaica, New York, N.Y. 11432

[21] Appl. No.: 744,678

[22] Filed: Nov. 24, 1976

[51] Int. Cl.² .................................................. B23Q 7/10
[52] U.S. Cl. ..................................... 29/809; 29/33 K; 29/563; 29/564.1; 29/789; 29/797; 140/147; 221/298
[58] Field of Search ................... 221/298; 29/429, 430, 29/33 K, 785, 789, 563, 564.1, 787, 792, 797, 795, 809, 818, 234; 140/147; 53/128, 367, 78

[56] References Cited

U.S. PATENT DOCUMENTS

| 427,093 | 5/1890 | Lennon | 221/298 X |
|---|---|---|---|
| 3,028,886 | 4/1962 | Drukker | 140/147 |
| 3,187,418 | 6/1965 | Kent | 29/785 X |
| 3,188,727 | 6/1965 | Davis | 29/785 X |
| 3,556,168 | 1/1971 | Baker | 140/147 X |
| 3,623,210 | 11/1971 | Shields | 29/429 |
| 3,747,648 | 7/1973 | Bauer | 140/147 |
| 3,842,533 | 10/1974 | Mayer | 221/298 X |

*Primary Examiner*—Victor A. DiPalma
*Attorney, Agent, or Firm*—C. Bruce Hamburg

[57] ABSTRACT

Apparatus for placing a sheath on a vertically oriented elongated member, the sheath having an open end for receiving the elongated member, comprises an upright magazine for containing a stacked plurality of the sheaths with the openings thereof oriented downwardly, a downwardly extending passage having an upper end communicating with the magazine and a lower end having a discharge opening arranged on a vertical axis with which the elongated member is to be aligned for being received in a respective said sheath discharged from the discharge opening onto the elongated member, a first gate defining the boundary between the magazine and the passage and for blocking transit of the sheath from the magazine into the passage and a second gate below the first gate a distance about equal to the length of a respective said sheath for blocking transit of the sheaths to the discharge opening of the passage, whereby the sheaths may be individually discharged by gravity onto respective said elongated members consecutively positioned in alignment with the axis by a cycle constituting closing the first gate of the loaded apparatus while the second gate is closed thereby to isolate the lowermost of the sheaths between the first and second gates, then opening the second gate thereby to permit the lowermost one of the sheaths of the stack to drop out of the discharge opening over the elongated member aligned with the axis, then closing the second gate and opening the first gate to permit the now lowermost one of the sheaths of the stack to descend onto the second gate, and repeating this cycle for each of the sheaths which is to be deposited on a respective elongated member. Apparatus for assuring the straightness of the elongated member thereby to facilitate the placing of a sheath on the elongated member comprises straightening means movable between an open inoperative condition and a closed operative condition for laterally engaging the elongated member at first, second and third consecutive positions along the length of the elongated member, the engaging at the first and third positions, on the one hand, and the engaging at the second position, on the other hand, being in opposition and holding the elongated member in a straight configuration, and means for effecting movement of the straightening means between the inoperative and operative conditions thereof.

3 Claims, 3 Drawing Figures

APPARATUS FOR HOLDING HYPODERMIC NEEDLES STRAIGHT AND PLACING SHEATHS THEREON

BACKGROUND OF THE INVENTION

This invention relates to apparatus for holding elongated members straight and placing sheaths thereon. The apparatus of the invention is particularly suited for the placing of sheaths on hypodermic needles but is not limited to such use in principle.

Apparatus such as that disclosed in U.S. Pat. No. 3,623,210 performs various operations on syringe sub-assemblies comprising a syringe vial or barrel and a hypodermic needle connected to one end thereof, such as washing the interior of the vial and applying a sheath to the needle. In U.S. Pat. No. 3,623,210, the sheath is received in a tubular member positioned on top of a pair of jaw levers and the placing of the sheath on the needle includes lowering the jaw levers over the needle. The orifice formed in the pair of closed jaw levers through which the needle passes into the sheath as the jaw levers are lowered is rather small and, consequently, the needle will sometimes engage the wall of the orifice which can dull and even form burrs on the pointed end of the needle. Moreover, should a particular needle be bent significantly out of vertical, the sheath placing in that case becomes entirely inoperative.

It is an object of the present invention to provide appratus which avoids these disadvantages of the prior art.

Other objects and advantages of the invention will be apparent to one skilled in the art from the following description thereof.

SUMMARY OF THE INVENTION

According to one aspect of the invention, there is provided apparatus for placing a sheath on a vertically oriented elongated member which apparatus avoids the possibility of contact of the elongated member, such as a hypodermic needle, with an element of the machinery whereby the elongated member could be damaged. The apparatus comprises an upright magazine for containing a stacked plurality of sheaths each having an open end for receiving the elongated member, the sheaths being stacked with the openings thereof oriented downwardy, a downwardly extending passage having an upper end communicating with the magazine and a lower end having a discharge opening arranged on a vertical axis with which the elongated member is to be aligned for being received in a respective one of the sheaths discharged from the discharge opening onto the elongated member, a first gate defining the boundary between the magazine and the passage and for blocking transit of the sheath from the magazine into the passage and a second gate below the first gate a distance about equal to the length of one of the sheaths for blocking transit of the sheaths to the discharge opening of the passage. With this apparatus, the sheaths may be individually discharged by gravity onto respective elongated members consecutively positioned in alignment with the axis of the discharge opening by a cycle constituting closing the first gate of the loaded apparatus while the second gate is closed thereby to isolate the lowermost of the sheaths between the first and second gates, then opening the second gate thereby to permit the lowermost one of the sheaths of the stack to drop out of the discharge opening over the elongated member aligned with the aforementioned axis, then closing the second gate and opening the first gate to permit the now lowermost one of the sheaths of the stack to descend onto the second gate. This cycle may be repeated for each sheath which is to be deposited on a respective elongated member.

The apparatus may include first and second hydraulic cylinder and piston assemblies mounted adjacent the passage with the axis of each thereof intersecting the passage and respective first and second openings communicating with the passage for permitting the pistons of the first and second assemblies to reciprocate relative to the passage, the pistons constituting the aforementioned gates.

According to another aspect to the invention, there is provided apparatus for assuring the straightness of the elongated member thereby to facilitate the placing of the sheath thereon. This apparatus comprises straightening means movable between an open inoperative condition and a closed operative condition for laterally engaging the elongated member at first, second and third consecutive positions along the length thereof, the engaging at the first and third positions, on the one hand, and the engaging at the second position, on the other hand, being in opposition and holding the elongated member in a straight configuration, and means for effecting movement of the straightening means between the inoperative and operative conditions thereof. The straightening means may comprise first and second clamping members, the first clamping member including means defining a pair of like notches which are vertically spaced parallel to the axis of the elongated member when the clamping members are closed and the second clamping member including means defining a notch similar to but opposite to the two notches of the first clamping member and being located between the two notches of the first clamping member when the clamping members are closed, the three notches being arranged to engage the elongated member at the respective three positions when the clamping members are closed thereby to hold the elongated member in a straight configuration. The means for effecting movement of the straightening means between the inoperative and operative conditions thereof may comprise means for pivoting the clamping members into and out of engagement with the elongated member.

When the sheath placing apparatus and elongated member straightness assuring apparatus are used in combination according to the invention, the straightening means are arranged to engage the elongated member below the upper end thereof thereby to leave a sufficient upper portion of the elongated member free for being received in the sheath when the elongated member is positioned below the discharge opening in alignment with the vertical axis thereof.

DESCRIPTION OF A PREFERRED EMBODIMENT

Figure 1:
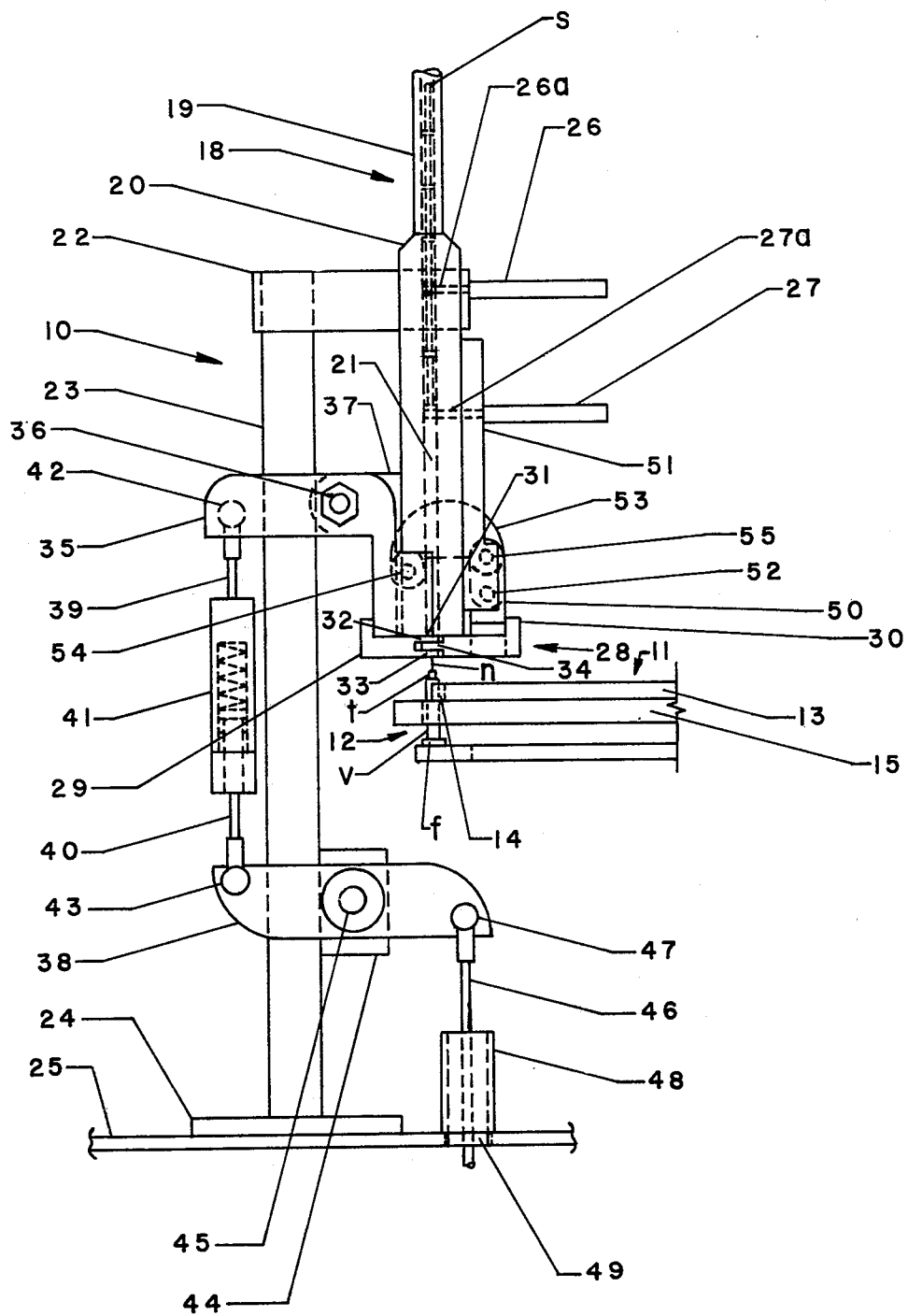
FIG. 1 is an elevation of an apparatus according to the invention in combination with a turret-type washing machine for syringe vial-needle sub-assemblies.

The illustrated apparatus 10 according to the invention is particularly intended for use in combination with a turret apparatus 11 (FIG. 1) of the type disclosed, for example, in U.S. Pat. No. 3,623,210 and constitutes improved means for placing the sheaths s on the hypodermic needles n of the syringe sub-assemblies 12 constituted of syringe barrels or vials v having a flange f at one end thereof and a needle n affixed to the other end thereof. A portion of the main turret of the apparatus 11 is illustrated, including a disc 13 which is rotationally indexed in the horizontal plane in which it is located, recesses 14 in the periphery of the disc 13 each adapted for receiving a respective syringe sub-assembly 12, an annular rail 15 for retaining the syringe sub-asemblies 12 in the recesses 14 and a lower annular rail 17 for supporting the syringe sub-assemblies 12 from below.

The sheaths s are fed from a stack thereof in a substantially vertical chute 18. The sheaths s are arranged in the chute 18 with the flanged open end thereof oriented downwards. The chute 18 is constituted of a first member 19 and a second member 20 through which members 19 and 20 a vertical passage 21 extends. The member 20 is connected to an arm 22 which is mounted on a post 23, the post 23 having a pedestal 24 which is mounted on a plate 25 below which a conventional drive train (not illustrated) is located.

Figure 2:
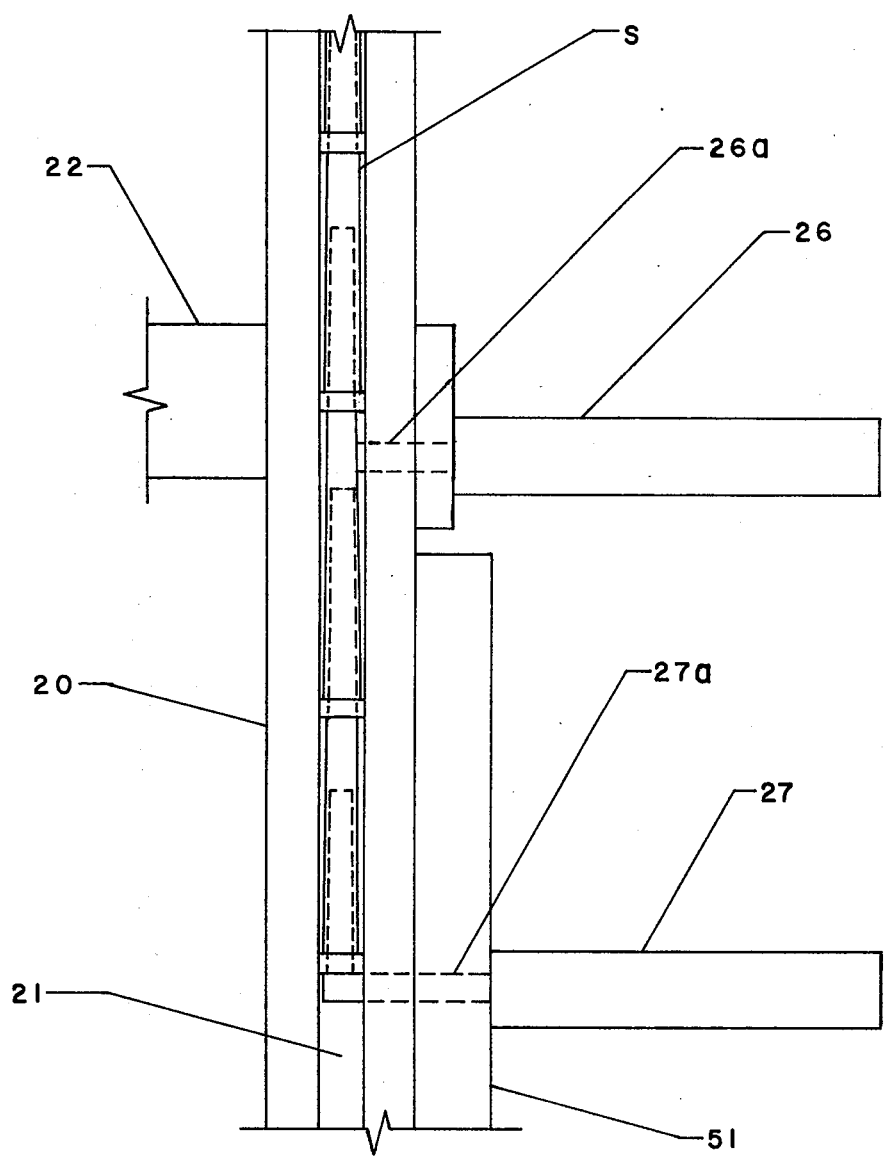
FIG. 2 is a detail of part of the structure of FIG. 1.

Upper and lower hydraulic cylinder and piston assemblies 26 and 27 are fixedly mounted relative to the member 20 for controlling the transit of the syringe sub-assemblies 12 through the passage 21. The axis of each of the cylinder and piston assemblies intersects the passage 21 perpendicularly to the axis of the passage 21. Respective bores permit reciprocation of the pistons 26a and 27a into and out of the passage 21. Functionally, therefor, the piston 26a serves as an upper gate and the piston 27a serves as a lower gate. The portion of the passage 21 up to the piston 26a may be regarded as a magazine. As seen in FIG. 1, and in enlarged detail in FIG. 2, the lowermost sheath rests on the piston 27a, which is extended into the passage 21 and, therefore, prevents the lowermost sheath from dropping out of the passage 21 onto the vertically disposed needle n which has been brought, as part of a syringe sub-assembly 12, into alignment with the axis of the passage 21 by indexed rotation of the disc 13 of the main turret of the apparatus 11. The next to bottom sheath is supported by the piston 26a. It can be seen that the distance between the pistons 26a and 27a is about equal to the length of a sheath. The piston 26a extends into the passage 21 a distance no greater than the difference between the radius of the main body of the sheath s and the radius of the flange f thereof so that the flange f rests on the piston 26a whereby the piston 26a supports the sheath but the piston does not pinch the top of the lowermost sheath. Consequently, when the piston 27a is then retracted out of the passage 21, the lowermost sheath is free to drop onto the needle n, the needle n being received into the sheath. The vial v has a throat t into which the needle n is received. The unstretched internal diameter of the main body of the rubber sheath s is slightly less than the external diameter of the throat t. When the sheath s is placed on the needle n by being dropped thereon by means of the apparatus of the invention, the main body of the sheath s will not descend over the throat t. However, indexed rotation of the disc 14 will carry the syringe sub-assembly 12 with the sheath s loosely placed thereon to another work station, not constituting part of the present invention, at which a pair of jaws will force the lower extremity of the sheath s over the throat t, the sheath s thereby becoming fastened to the syringe sub-assembly sufficiently that it will stay on the throat t and, consequently, the needle n when the needle is pointed downward but can be removed manually when the syringe is to be used.

With the lowermost sheath being discharged onto the needle of a syringe sub-assembly and that syringe sub-assembly being rotationally indexed away from this station while another syringe sub-assembly on the needle of which a sheath is to be placed is rotationally indexed into this station, it is necessary to have the new lowermost sheath ready for discharge. The piston 26a is retracted out of the passage 21 so that the stack of sheaths drops down a distance about equal to the length of a single sheath, the new lowermost sheath now resting on the piston 27a which was extended back into the passage 21 right after the previous lowermost sheath was released. The piston 26a is then returned to its extended position. Retraction of the piston 27a at this pont will result in discharge of only the new lowermost sheath. Hence, the complete cycle has been described. Means for automatically cyclically operating hydraulic cylinder-piston assemblies have not been illustrated herein because such means are well known, such as cam-actuated means as disclosed in U.S. Pat. No. 3,623,210.

Positioned below the discharge end of the passage 21 are the working components of apparatus 28 for assuring the straightness of the needle n thereby to facilitate the placing of the sheath s on the needle n. These working components or straightening means are in the form of two clamping members 29 and 30. The two clamping members 29 and 30 include means for engaging the needle n at three positions along the length thereof on a vertical axis thereby to assure that the needle is oriented vertically straight upward in alignment with the axis of the discharge opening of the passage 21. When the apparatus 28 is used in conjunction with the sheath discharging apparatus, as illustrated herein, the clamping members 29 and 30 have been closed on the needle n before the piston 27a is retracted to release the lowermost sheath s. A substantial portion of the needle n extends above the closed clamping members 29 and 30. When the sheath s is released, it drops over that portion of the needle n and the flange f of the sheath s rests on the top surface 31 of the clamping member 29. The clamping members 29 and 30 are then swung open and the sheath s drops down so that the flange portion thereof is received on the throat t of the vial v. The disc 14 then indexes rotationally bringing the syringe sub-assembly 12 on which a sheath s has just been placed to a station at which the lower portion of the sheath s will be pushed completely down over the throat t and bringing the next syringe sub-assembly to the illustrated station at which a sheath is to be placed on the needle thereof. The clamping members 29 and 30 are then closed on the needle of this assembly and another cycle of sheath placement is affected.

Figure 3:
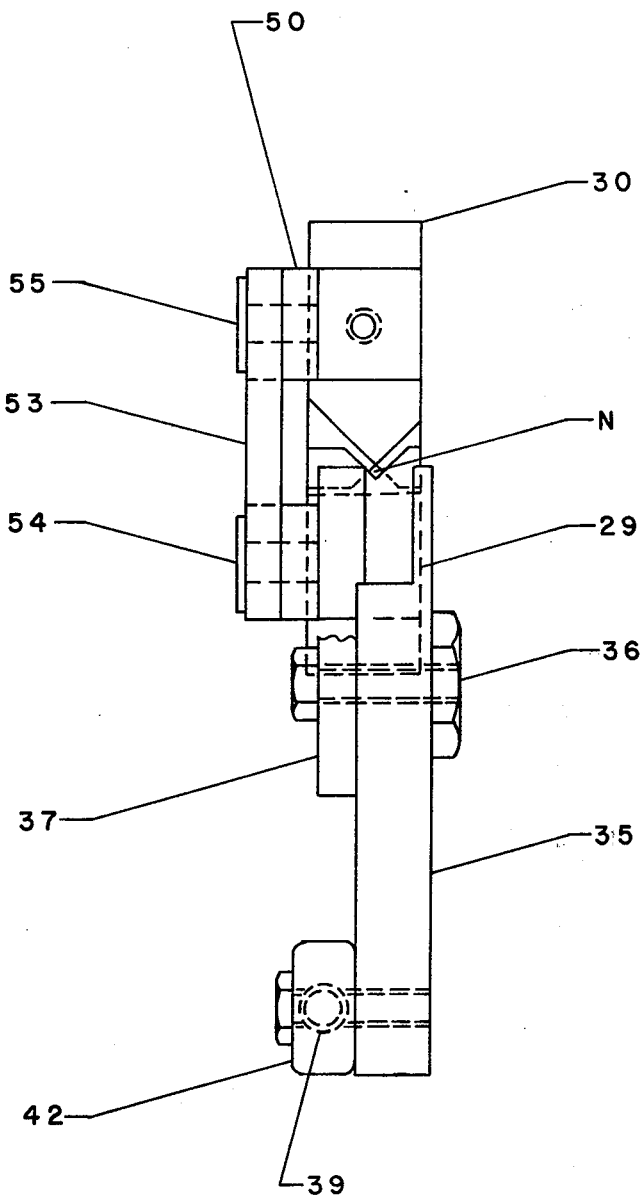
FIG. 3 is a plan view of a detail of part of the structure of FIG. 1.

The clamping member 29 has two tongues 32 and 33 which are vertically spaced in horizontal planes when the clamping members are closed, and the clamping member 30 has a single tongue 34 which is in a horizontal plane when the clamping members are closed. The tongue 34 is received between the tongues 32 and 33 when the clamping members are closed. Each of the tongues 32, 33 and 34 has a respective V-shaped notch formed therein (FIG. 3). The notches in tongues 32 and 33 are vertically aligned when the clamping members are closed so that the notch in the tongue 33, which is identical to the notch in the tongue 32, does not show in FIG. 3. Each of the notches forms a right angle and the notches in the tongues 32 and 33 are opposed to the notch in tongue 34 when the clamping members are closed so that, in plan view, the notches form a square the length of a side of which is about equal to the diameter of the needle n. It can, therefore, be understood that the respective notches in tongues 32, 34 and 33 contact the needle n at three consecutive locations downwardly along the length thereof in that order, the contacting of the needle n by the notches in the tongues 32 and 33 being in opposition to the contacting of the needle n by the notch in the tongue 34 whereby the needle n is held in a straight, vertical orientation.

The clamping member 29 is rigidly mounted on one end of a right-angled lever 35. The lever 35 is supported by a pivotal connection to an arm 37 rigidly mounted on the chute member 20. The other end of the lever 35 is pivotally connected to one end of a lever 38 by means of tie rods 39 and 40 having a shock absorber or dampener 41 interposed therebetween, the tie rod 39 being fastened to the lever 35 by means of a pivotal connection 42 and the tie rod 43 being fastened to the lever 38 by means of a pivotal connection 43. At a point intermediate its ends, the lever 38 is mounted on an ear 44 on the post 23 by means of a pivotal connection 45. A tie rod 46 is connected to the other end of the lever 38 by means of a pivotal connection 47. The tie rod 46 passes through a tubular housing 48 surrounding an opening 49 through the plate 25. The tie rod 46 is cam-actuated by conventional means (not illustrated) in a downward stroke from the position illustrated in FIG. 1 to open the clamping members 29 and 30 and in a return upward stroke to close the clamping members again. It is obvious how the motion of the clamping member 29 is effected from the foregoing description of the linkage between the tie rod 46 and the clamping member 29.

A linkage is provided between the clamping member 29 and the clamping member 30 so that these members swing outwards and inwards in unison to effect the opening and closing. An arm 50 on which the clamping member 30 is rigidly mounted is connected to the lower portion of a block 51 by means of a pivotal connection 52, the block 51 being rigidly connected to the member 20. An arm 53 is pivotally connected at one end to the lever 35 between the pivotal connection 36 and the clamping member 29 by means of a pivotal connection 54 and is pivotally connected at the other end to the arm 50 by means of a pivotal connection 55. As clockwise (as viewed in FIG. 1) pivoting of the lever 35 around the pivotal connection 36 causes the clamping member 29 to swing away from the needle n the arm 50 carrying the clamping member 30 is pivoted in the counterclockwise direction (as viewed in FIG. 1) around the pivotal connection 52, thereby swinging the clamping member 30 away from the needle n, due to the linkage of the lever 35 to the arm 50 through the arm 53 pivotally connected at one end to the lever 35 and at the other end to the arm 50. This action reverses, of course, to cause the clamping member 30 to swing toward the needle n as the clamping member 29 is swung toward the needle n by counterclockwise (as viewed in FIG. 1) rotation of the lever 35 about the pivotal connection 36.

While the invention has been described by reference to a particular embodiment thereof, it is to be understood that such description is for the purpose of illustration rather than limitation of the invention defined by the hereto appended claims, which claims are intended to include all variations and modifications which would have been obvious to one of ordinary skill in the art.

What is claimed is:

1. The combination of apparatus for placing a sheath on a vertically oriented hypodermic needle, the sheath having an open end for receiving the hypodermic needle, and apparatus for assuring the straightness of the hypodermic needle thereby to facilitate the placing of the sheath on said hypodermic needle, the sheath placing apparatus comprising an upright magazine for containing a stacked plurality of the sheaths with the openings thereof oriented downwardly, a downwardly extending passage having an upper end communicating with the magazine and a lower end having a discharge opening arranged on a vertical axis with which the hypodermic needle is to be aligned for being received in a respective said sheath discharged from the discharge opening onto the hypodermic needle, a first gate defining the boundary between the magazine and the passage and for blocking transit of a sheath from the magazine into the passage and a second gate below the first gate a distance about equal to the length of a respective said sheath for blocking transit of said sheaths to the discharge opening of the passage, whereby said sheaths may be individually discharged by gravity onto respective said hypodermic needles consecutively positioned in alignment with said axis by a cycle constituting closing the first gate of the loaded apparatus while the second gate is closed thereby to isolate the lowermost of said sheaths between said first and second gates, then opening the second gate thereby to permit the lowermost one of said sheaths of said stack to drop out of the discharge opening over the hypodermic needle aligned with said axis, then closing the second gate and opening the first gate to permit the now lowermost one of said sheaths of the stack to descend onto the second gate, and repeating said cycle for each said sheath which is to be deposited on a respective said hypodermic needle, and the straightness assuring apparatus comprising straightening means movable between an open inoperative condition and a closed operative condition for engaging said hypodermic needle with only point contact at first, second and third consecutive positions along the length of said hypodermic needle, said engaging at said first and third positions, on the one hand, and said engaging at said second position, on the other hand, being in opposition and holding the hypodermic needle in a straight configuration, and means for effecting movement of said straightening means between said inoperative and operative conditions thereof, said straightening means comprising first and second clamping members, said first clamping member including means defining a pair of like substantially right-angled notches which are vertically spaced and vertically aligned throughout on lines parallel to the axis of the elongated member when the clamping members are closed and said second clamping member including means defining a substantially right-angled notch similar to but opposite to the two notches of said first clamping member and being located between the two notches of said first clamping member when the clamping members are closed, said three notches being arranged to engage said hypodermic needle at the respective said three positions when said clamping members are closed thereby to hold the hypodermic needle in a straight configuration, the two notches of said first clamping member being arranged to engage the hypodermic needle at each of said first and third positions only at two points each rotationally spaced from the other by substantially ninety degrees and the notch of said second clamping member being arranged to engage the hypodermic needle at said second position only at two points each rotationally spaced from the other by substantially ninety degrees and each rotationally spaced by substantially ninety degrees from a respective one of the points of contact of either of said notches of said first clamping member with the needle.

2. Apparatus according to claim 1, comprising first and second hydraulic cylinder and piston assemblies mounted adjacent said passage with the axis of each thereof intersecting said passage and respective first and second openings communicating with said passage for permitting the pistons of the first and second assemblies to reciprocate relative to said passage, said pistons constituting said gates.

3. Apparatus according to claim 1, in which said means for effecting movement comprises means for pivoting said clamping members into and out of engagement with said elongated member.

* * * * *